(12) United States Patent
Yamada

(10) Patent No.: US 11,478,149 B2
(45) Date of Patent: Oct. 25, 2022

(54) BRAIN FUNCTION MEASUREMENT DEVICE AND BRAIN FUNCTION MEASUREMENT METHOD

(71) Applicant: National Institute of Advanced Industrial Science and Technology, Tokyo (JP)

(72) Inventor: Toru Yamada, Ibaraki (JP)

(73) Assignee: National Institute of Advanced Indusuial Science and Technology, Tokyo (JP)

( * ) Notice: Subject to any disclaimer, the term of this patent is extended or adjusted under 35 U.S.C. 154(b) by 213 days.

(21) Appl. No.: 16/603,756

(22) PCT Filed: Mar. 28, 2018

(86) PCT No.: PCT/JP2018/012853
§ 371 (c)(1),
(2) Date: Oct. 8, 2019

(87) PCT Pub. No.: WO2018/190130
PCT Pub. Date: Oct. 18, 2018

(65) Prior Publication Data
US 2020/0029819 A1    Jan. 30, 2020

(30) Foreign Application Priority Data
Apr. 14, 2017 (JP) .............................. JP2017-080533

(51) Int. Cl.
*A61B 5/00* (2006.01)

(52) U.S. Cl.
CPC .......... *A61B 5/0082* (2013.01); *A61B 5/6814* (2013.01)

(58) Field of Classification Search
None
See application file for complete search history.

(56) References Cited

U.S. PATENT DOCUMENTS

| 5,803,909 A | 9/1998 | Maki et al. |
| 2015/0173618 A1 | 6/2015 | Kusukame |
| 2018/0028098 A1* | 2/2018 | Yamada ............... A61B 5/4064 |

FOREIGN PATENT DOCUMENTS

| JP | 2009-268707 A | 11/2009 |
| WO | 2016/132989 A1 | 8/2016 |

* cited by examiner

Primary Examiner — Yi-Shan Yang
(74) Attorney, Agent, or Firm — Hoffmann & Baron, LLP

(57) ABSTRACT

Brain function measurement device including: first light-irradiation probe to irradiate a brain of a subject with light; first light-detection probe to detect light reflected by the brain among the light from the first light-irradiation probe; second light-irradiation probe to irradiate the brain with light; second light-detection probe to detect light reflected by the brain among the light from the second light-irradiation probe; and control unit configured to adjust a light amount irradiated by the second light-irradiation probe so that the light amount measured with respect to a channel between the first light-detection and the second light-irradiation probes becomes an observation value with respect to a channel between the first light-irradiation and the first light-detection probes, and to adjust a light amount detected by the second light-detection probe so that the light amount measured with respect to a channel between the second light-irradiation and the second light-detection probes becomes the observation value.

12 Claims, 7 Drawing Sheets

BRAIN FUNCTION MEASUREMENT DEVICE AND BRAIN FUNCTION MEASUREMENT METHOD

CROSS-REFERENCE TO RELATED APPLICATIONS

This application is the U.S. National Phase of International Patent Application No. PCT/JP2018/012853, filed 28 Mar. 2018, the contents of which are incorporated herein by reference in its entirety.

BACKGROUND

Technical Field

The present invention relates to a device and a method for measuring brain functions.

Related Art

In recent years, as a simple brain-function measurement technique, functional near-infrared spectroscopy (fNIRS) has been known. Measurement using fNIRS is performed with probes attached to the scalp. Accordingly, depending on the amount of hair immediately under the probes, or the degree of adhesion between the probes and the scalp, the magnitude of optical attenuation that occurs between the scalp and the probes varies. Thus, the signal-to-noise ratio also varies significantly from one measurement point (channel) to another, and it is impossible to apply strict statistical analysis to the measured signal.

Against this background, a technique has been devised with which, as indicated in Patent Literature 1, the noise variance of all signals measured in each channel is equalized. That is, the technique involves introducing optical attenuators between the respective light sources or detectors and the living body, and controlling the optical transmittance of the optical attenuators so as to level the observed light amounts in all channels, thereby leveling the noise variance. The optical transmittance of each optical attenuator is set based on a measurement value.

CITATION LIST

Patent Literature

Patent Literature 1: WO2016132989.

SUMMARY

Technical Problem

The technique indicated in Patent Literature 1 has the problem that it is necessary to perform as accurate a calibration as possible with respect to all of the optical attenuators.

The present invention has been made to solve the problem, and an object of the present invention is to provide a brain function measurement device and a brain function measurement method with which it is possible to eliminate or minimize the need for a calibration operation.

Solution to Problem

In order to solve the problem, the present invention provides a brain function measurement device including: a first irradiation means which irradiates a brain of a subject with light; a first detection means which is disposed adjacent to the first irradiation means and detects light reflected by the brain among the light irradiated in a first direction from the first irradiation means; a second irradiation means which is disposed adjacent to the first detection means and irradiates the brain of the subject with light; a second detection means which is disposed adjacent to the second irradiation means and detects light reflected by the brain among the light irradiated from the second irradiation means; and a control means that adjusts a light amount irradiated by the second irradiation means so that a light amount measured with respect to a measurement point between the first detection means and the second irradiation means becomes an observation value observed with respect to a measurement point between the first irradiation means and the first detection means, and that adjusts a light amount detected by the second detection means so that a light amount measured with respect to a measurement point between the second irradiation means and the second detection means becomes the observation value.

In order to solve the problem, the present invention also provides a brain function measurement method of measuring brain function by irradiating a brain of a subject with light and detecting light reflected by the brain, the method including: a first step of adjusting a light amount irradiated by a second irradiation means so that a light amount measured with respect to a measurement point between a first detection means and the second irradiation means adjacent to each other becomes an observation value observed with respect to a measurement point between a first irradiation means adjacent to the first detection means and the first detection means; and a second step of adjusting the light amount detected by a second detection means so that a light amount measured with respect to a measurement point between the second irradiation means and the second detection means adjacent to the second irradiation means becomes the observation value.

Advantageous Effects of Invention

According to the present invention, it is possible to provide a brain function measurement device and a brain function measurement method with which the need for a calibration operation can be eliminated or minimized.

DETAILED DESCRIPTION

In the following, embodiments of the present invention will be described in detail with reference to the drawings, wherein similar signs designate similar or corresponding portions.

Figure 1:
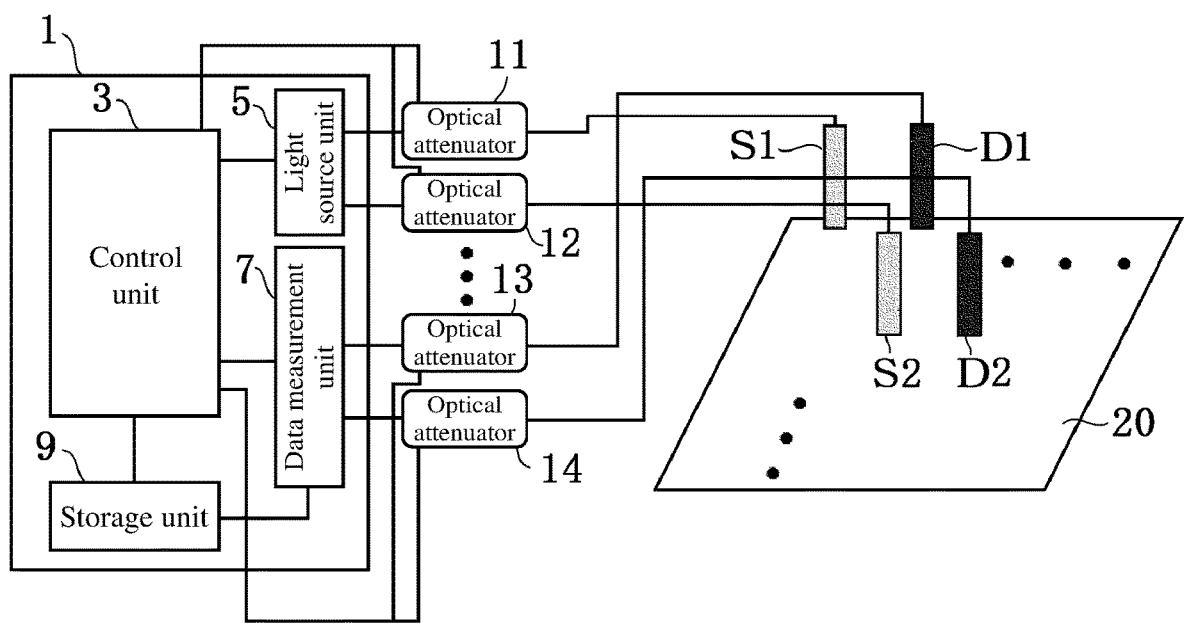
FIG. 1 depicts a configuration of a brain function measurement system according to an embodiment of the present invention.

FIG. 1 depicts a configuration of a brain function measurement system according to an embodiment of the present invention. As depicted in FIG. 1, the brain function measurement system is provided with: a brain function measurement device 1 including a control unit 3, a light source unit 5, a data measurement unit 7, and a storage unit 9; and a holder 20 including optical attenuators 11 to 14, and light irradiation probes S1, S2 and light detection probes D1, D2 that are attached to the subject.

The control unit 3 is connected to the light source unit 5, the data measurement unit 7, the storage unit 9, and the optical attenuators 11 to 14. The light irradiation probes S1, S2 are connected to the light source unit 5 via the optical attenuators 11, 12, respectively. The light detection probes D1, D2 are connected to the data measurement unit 7 via the optical attenuators 13, 14, respectively. The data measurement unit 7 is also connected to the storage unit 9.

Figure 2:
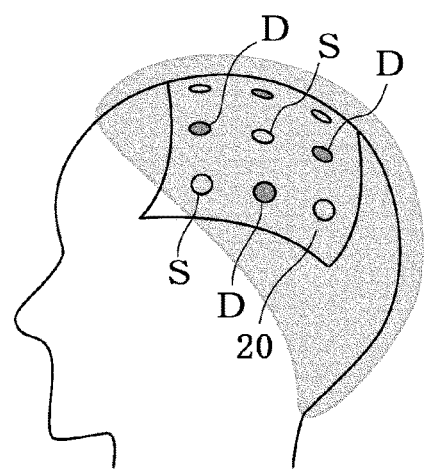
FIG. 2 depicts a first arrangement example of light irradiation probes S1, S2 and light detection probes D1, D2 on a holder 20 depicted in FIG. 1.

Meanwhile, the light irradiation probes S1, S2, for example, on the holder 20 depicted in FIG. 1 are arranged at the positions of light irradiation probes S indicated by white circles in FIG. 2. The light detection probes D1, D2 on the holder 20 depicted in FIG. 1 are arranged at the positions of light detection probes D indicated by black circles in FIG. 2. In FIG. 2, the grey portion indicates hair; the same applies in FIG. 5 and FIG. 8.

Figure 3:
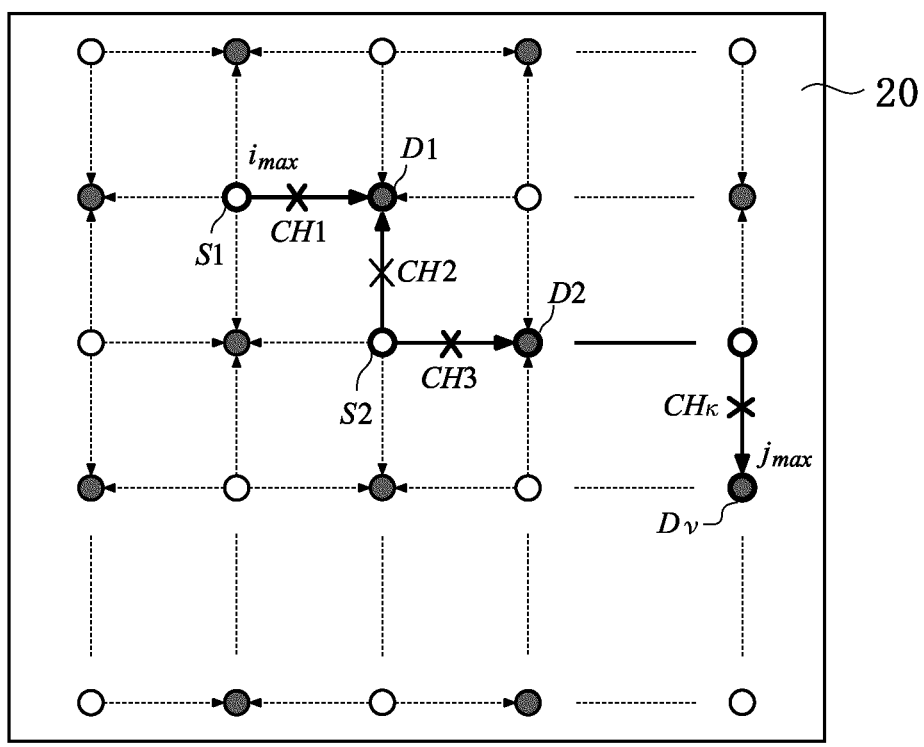
FIG. 3 is a schematic diagram illustrating the arrangement of the light irradiation probes S and the light detection probes D depicted in FIG. 2 in a two-dimensional plane.

Referring to FIG. 2, the light irradiation probes S and the light detection probes D are arranged alternately, as illustrated by a schematic diagram of FIG. 3, for example.

Noise Levelling in Linked Channel Group

Figure 4:
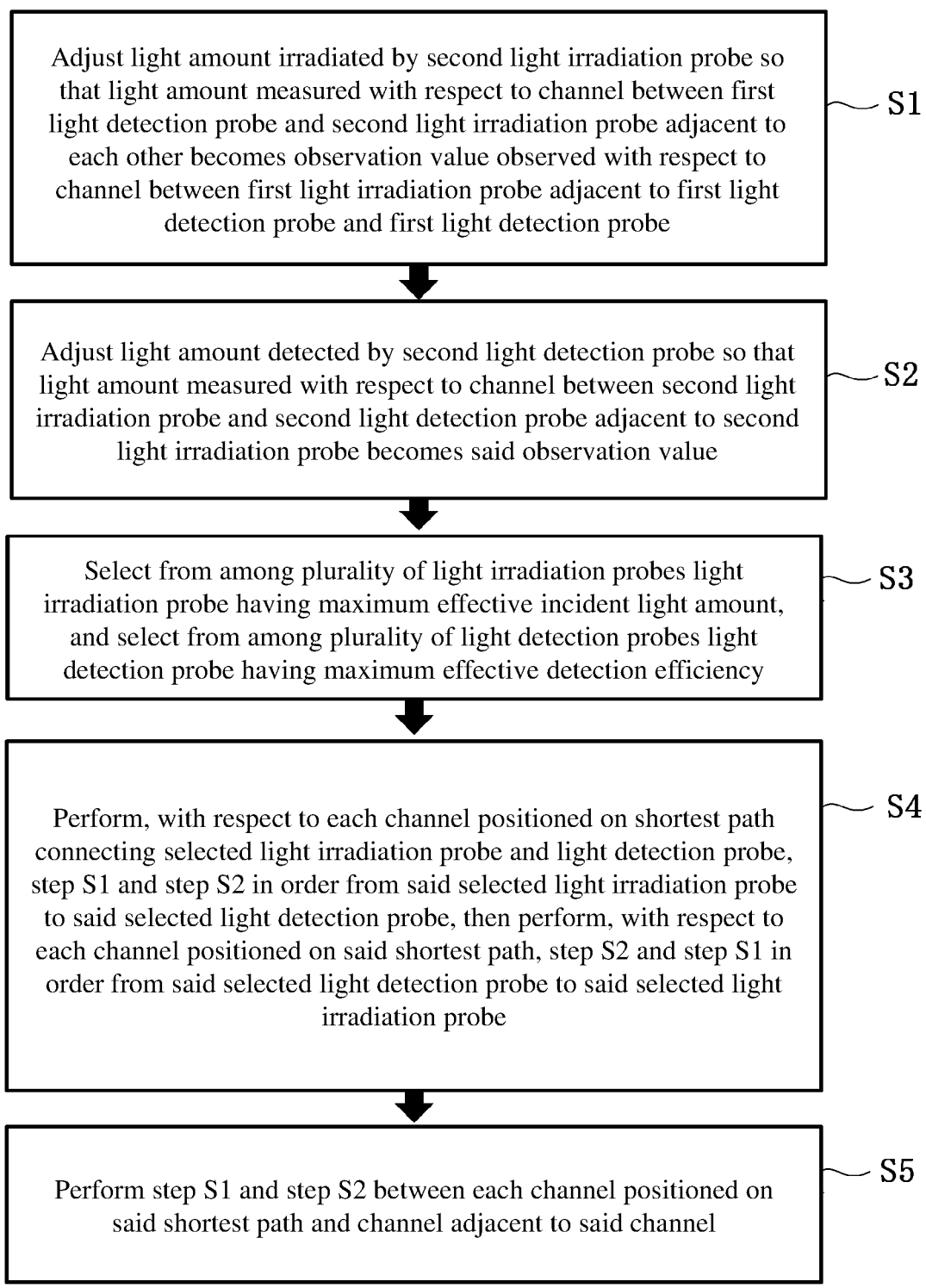
FIG. 4 is a flowchart illustrating a method of implementing a first brain function measurement method according to an embodiment of the present invention through control by a control unit 3 depicted in FIG. 1.

FIG. 4 is a flowchart illustrating a method of implementing a first brain function measurement method according to an embodiment of the present invention through control by the control unit 3 depicted in FIG. 1. In the following, with reference to FIG. 3, the first brain function measurement method of FIG. 4 will be described. It goes without saying that the first brain function measurement method of FIG. 4 depicted in FIG. 1 is not limited to the case of implementation through control by the control unit 3.

In step S1, the control unit 3 adjusts the light amount detected by the second light detection probe D2 by controlling the optical attenuator 12 connected to the second light irradiation probe S2 so that the light amount measured by the first light detection probe D1 with respect to a channel CH2 between the first light detection probe D1 and the second light irradiation probe S2 adjacent to each other becomes the value (observation value) of the light amount observed by the first light detection probe D1 with respect to a channel CH1 between the first light irradiation probe S1 adjacent to the first light detection probe D1 and the first light detection probe D1.

Then, in step S2, the control unit 3 adjusts the light amount detected by the second light detection probe D2 by controlling the optical attenuator 14 so that the light amount measured by the second light detection probe D2 with respect to a channel CH3 between the second light irradiation probe S2 and the second light detection probe D2 adjacent to the second light irradiation probe S2 becomes the observation value.

Then, in step S3, the control unit 3 selects from a plurality of light irradiation probes a light irradiation probe having a maximum effective incident light amount, and selects from a plurality of light detection probes a light detection probe having a maximum effective detection efficiency.

Then, in step S4, the control unit 3 performs, with respect to each of channels positioned on a shortest path connecting the light irradiation probe and the light detection probe that have been selected in step S3, step S1 and step S2 in the order of from the selected light irradiation probe to the selected light detection probe, and thereafter performs, with respect to each of the channels on the shortest path, step S2 and step S1 in the order from the selected light detection probe to the selected light irradiation probe.

Then, in step S5, the control unit 3 performs step S1 and step S2 between each of the channels positioned on the shortest path and a channel adjacent to said channel. In the following, a concrete example of the first brain function measurement method of FIG. 4 will be described.

With respect to a channel k, the observed light amount J at each wavelength λ is expressed by the following Expression (1):

[Mathematical formula 1]

$$J_{k,\lambda} = I_{i,\lambda} a_i r_{i,0,\lambda} R r_{j,0,\lambda} a_j \quad (1)$$

In the above, $r_{i,0,\lambda}$ means a time-averaged value of optical transmittance between the light irradiation probe and the scalp; $r_{j,0,\lambda}$ means a time-averaged value of optical transmittance between the light detection probe and the scalp; and R means a time-averaged value of tissue transmittance.

Any one of the optical attenuators 11 to 14 depicted in FIG. 1 is connected to one of n light irradiation probes and m light detector probes constituting multiple channels, wherein the optical attenuators connected to the light irradiation probes have transmittance ai (where i is 1 or more and n or less, ai is 0 or more and 1 or less), and the optical attenuators connected to the light detection probes have transmittance aj (where j is (n+1) or more and (n+m) or less, aj is 0 or more and 1 or less). In this case, the magnitude h of noise included in an fNIRS signal in the channel k is expressed by the following Expression (2):

[Mathematical formula 2]

$$h_{k,\lambda}(t) = n_{j,\lambda}(t) / J_{k,\lambda} \quad (2)$$

In the above, $n_{j,\lambda}(t)$ represents detector noise generated during measurement with a light detector probe j; differences between probes can be virtually disregarded when the detectors of the same standard are used. Thus, with reference to Expression (2), it is seen that levelling the magnitude h of noise included in the fNIRS signal between channels means levelling the observed light amount $J_{k,\lambda}$ in each channel.

Taking the logarithm of both sides of Expression (1) yields the following Expression (3):

[Mathematical formula 3]

$$\log J_{k,\lambda} = \log(I_{i,\lambda,l} a_i r_{i,0,\lambda,l} C_1) + \log(r_{j,0,\lambda,l} a_j C_2) \quad (3)$$

The coefficient $C_1$ and coefficient $C_2$ of Expression (3) satisfy the relationship of the following Expression (4):

[Mathematical formula 4]

$$C_1 C_2 = R \quad (4)$$

In the following, $I_{i,\lambda,l} a_i r_{i,0,\lambda,l}$ in the first term of Expression (3) will be referred to as effective incident light amount, and $r_{j,0,\lambda,l} a_j$ in the second term will be referred to as effective detection efficiency.

Herein, the relationship between N measurement channels and the probes constituting the same is represented by a matrix G called a probe arrangement matrix. The matrix G is an N× (n+m) matrix of which the element g, when the light irradiation probe i and the light detector probe j constitute the channel k, is defined by the following Expression (5):

[Mathematical formula 5]

$$g_{kl} = \begin{cases} 1 & \text{When } l = i \text{ or } l = j \\ 0 & \text{Other cases} \end{cases} \quad (5)$$

Regardless of the scale or pattern of the channel or the arrangement of the probes, there is always only one matrix G that is determined correspondingly, and there is also always one pseudo-inverse matrix $G^+$ of the matrix G that is determined correspondingly. With the probe arrangement matrix, it is possible to summarize the relationship of Expression (3) with respect to an arbitrary channel into a matrix operation according to the following Expression (6):

[Mathematical formula 6]

$$s_\lambda = G \rho_\lambda \quad (6)$$

In the above, $s_\lambda$ is a column vector having the logarithm $\log J_{k,\lambda}$ (where k is 1 or more and N or less) of the observed light amount as an element, and is determined by actual measurement. On the other hand, $\rho_\lambda$ is a column vector represented by the following Expression (7) having, as the elements, the term $\log (I_{i,\lambda} a_i r_{i,0,\lambda} C_1)$ (where i is 1 or more and n or less) relating to the effective incident light amount to be estimated, and the term $\log (r_{j,0,\lambda,l} a_j C_2)$ (where j is (n+1) or more and (n+m) or less) relating to effective detection efficiency.

[Mathematical formula 7]

$$\rho_\lambda = \begin{pmatrix} \log(I_{1,\lambda} a_1 r_{1,0,\lambda} C_1) \\ \vdots \\ \log(I_{n,\lambda} a_n r_{n,0,\lambda} C_1) \\ \log(r_{n+1,0,\lambda} a_{n+1} C_2) \\ \vdots \\ \log(r_{n+m,0,\lambda} a_{n+m} C_2) \end{pmatrix} \quad (7)$$

Herein, by multiplying the Expression (7) with the pseudo-inverse matrix $G^+$ from the left, a particular solution to $\rho_\lambda$ is determined according to the following Expression (8):

[Mathematical formula 8]

$$G^+ s_\lambda = \begin{pmatrix} b_{1,\lambda} \\ \vdots \\ b_{n,\lambda} \\ b_{n+1,\lambda} \\ \vdots \\ b_{n+m,\lambda} \end{pmatrix} \quad (8)$$

Comparing Expression (7) with Expression (8) yields the relationships of the following Expression (9) and Expression (10):

[Mathematical formula 9]

$$I_{i,\lambda} a_i r_{i,0,\lambda} C_1 = e^{bi,\lambda} \quad (9)$$

[Mathematical formula 10]

$$r_{j,0,\lambda} a_j C_2 = e^{bj,\lambda} \quad (10)$$

In this way, the observed light amount $J_{k,\lambda}$ for each channel is obtained, and when the matrix G designating the channel arrangement is known, it is possible to determine the effective incident light amount of each light irradiation probe and the effective detection efficiency of each light detection probe as $e^{bi,\lambda}/C_1$, $e^{bj,\lambda}/C_2$, respectively.

In order to level the observed light amount, it is necessary to know not only the observed light amount but also the effective incident light amount and the effective detection efficiency for the following reason. The observed light amount is the product of the effective incident light amount and the effective detection efficiency. Even if there is a channel having a significantly different effective incident light amount, an apparently equal observed light amount may be indicated if the channel has a corresponding effective detection efficiency. Meanwhile, if there is even just one effective incident light amount exceeding a safe reference light amount, it cannot be said that the multiple channel measurement is being done safely. Accordingly, in order to confirm that the living body tissue is being irradiated with an amount of light less than or equal to the safe reference light amount, it is necessary to monitor the effective incident light amount.

Now, in the multiple-channel probe arrangement depicted in FIG. 3, it is possible to select, based on Expression (8), a light irradiation probe $i_{max}$ having a maximum effective incident light amount and a light detection probe $j_{max}$ having a maximum effective detection efficiency. Herein, it is assumed that the shortest path connecting the light irradiation probe $i_{max}$ and the light detection probe $j_{max}$ is configured of ν light irradiation probes and ν light detection probes, and levelling of the observed light amounts in (2ν−1) channels on the path will be described.

The light irradiation probes in the path are designated with signs S1, S2, . . . , Sν; the light detection probes are designated with signs D1, D2, . . . , Dν; and the respective channels are designated with signs CH1, CH2, . . . , CHκ (where κ=2ν−1). Thus, in FIG. 3, S1 indicates the light irradiation probe $i_{max}$, and Dν indicates the light detection probe $j_{max}$.

In the following, for simplicity of illustration, only the channels CH1 to CH3 will be considered. In this case, the content of Expression (6) can be rewritten as Expression (11):

[Mathematical formula 11]

$$\begin{pmatrix} s_{CH1} \\ s_{CH2} \\ s_{CH3} \end{pmatrix} = \begin{pmatrix} 1 & 0 & 1 & 0 \\ 0 & 1 & 1 & 0 \\ 0 & 1 & 0 & 1 \end{pmatrix} \begin{pmatrix} \rho_{S1} \\ \rho_{S2} \\ \rho_{D1} \\ \rho_{D2} \end{pmatrix} \quad (11)$$

In Expression (11), with respect to $S_{CH1}$ to $S_{CH3}$, measurement values can be calculated successively. Herein, it is contemplated to equalize $S_{CH2}$ and $S_{CH3}$ with the observation value of $S_{CH1}/S_{CH1}$. First, while monitoring the observed light amounts of channel CH1 and channel CH2, the optical attenuator 12 connected to the light irradiation probe S2 is controlled so that $S_{CH2}$ becomes the observation value/$S_{CH1}$. In this way, it becomes possible to achieve a state expressed by the following Expression (12):

[Mathematical formula 12]

$$\begin{pmatrix} s_{CH1} \\ s_{CH2} \\ s_{CH3} \end{pmatrix} \rightarrow \begin{pmatrix} \hat{s}_{CH1} \\ \hat{s}_{CH1} \\ \hat{s}_{CH3} \end{pmatrix} = \begin{pmatrix} 1 & 0 & 1 & 0 \\ 0 & 1 & 1 & 0 \\ 0 & 1 & 0 & 1 \end{pmatrix} \begin{pmatrix} \rho_{S1} \\ \rho'_{S2} \\ \rho_{D1} \\ \rho_{D2} \end{pmatrix} \quad (12)$$

Then, while monitoring the observed light amounts in channel CH2 and channel CH3, the optical attenuator 14 connected to the light detection probe D2 is controlled so that $S_{CH3}$ becomes the observation value/$S_{CH1}$. Through such control, it becomes possible to achieve a state expressed by the following Expression (13):

[Mathematical formula 13]

$$\begin{pmatrix} s_{CH1} \\ s_{CH2} \\ s_{CH3} \end{pmatrix} \rightarrow \begin{pmatrix} \hat{s}_{CH1} \\ \hat{s}_{CH1} \\ \hat{s}_{CH1} \end{pmatrix} = \begin{pmatrix} 1 & 0 & 1 & 0 \\ 0 & 1 & 1 & 0 \\ 0 & 1 & 0 & 1 \end{pmatrix} \begin{pmatrix} \rho_{S1} \\ \rho'_{S2} \\ \rho_{D1} \\ \rho'_{D2} \end{pmatrix} \quad (13)$$

Herein, a necessary and sufficient condition for Expression (13) to be valid is expressed by the following Expression (14):

[Mathematical formula 14]

$$\rho_{S1} = \rho'_{S2}, \rho_{D1} = \rho'_{D2} \quad (14)$$

Thus, it is seen that, through the series of operations described above, the observed light amounts are levelled to $e^{(\rho S1 + \rho D1)}$ in channels CH1 to CH3, and that the effective incident light amounts of all of the light irradiation probes and the effective detection efficiencies of all of the detection probes are respectively levelled to $e^{\rho S1}$, $e^{\rho D1}$. The present operation is a core means for achieving noise levelling without controlling the transmittances $a_i$, $a_j$ to designated values, and the operation will be hereafter referred to as an adjacent channel levelling operation. Referring to FIG. 3, by expanding the adjacent channel levelling operation from channel CH4 (not illustrated) onto channel CHv, it becomes possible to perform levelling in all of the channels CH1 to CHv.

Thus, with the levelling operation between adjacent channels, it is possible to perform levelling for adjacent channels or probes in accordance with the observed light amount of a reference-point channel, or the effective incident light amount or the effective detection efficiency of the light irradiation probe or the light detection probe that constitutes that channel. The adjacent channel levelling operation can be expanded onto a channel linked via a light irradiation probe or a light detection probe. The multiple channels configured by such linking will be referred to as a linked channel group.

In the above operation, the effective detection efficiencies of a series of light detection probes are levelled to $e^{\rho D1}$. However, because the effective detection efficiency of the light detection probe Dv constituting the channel CHv is the highest among all of the light detection probes, $e^{\rho Dv}$ is obviously greater than $e^{\rho D1}$. Accordingly, in order to maximize the observed light amount and level the noise to the maximum achievable S/N ratio, it is necessary to level the effective detection efficiency of each light detection probe to $e^{\rho Dv}$. In the following, this operation will be described.

In order to achieve the purpose, the adjacent channel levelling operation is terminated at the point in time that the channel CH($\kappa$−1) has been reached. The state at this point in time may be described, with respect to only the interval between channel CH($\kappa$−2) to channel CH$\kappa$ for sake of simplicity, by the following Expression (15):

[Mathematical formula 15]

$$\begin{pmatrix} s_{CH(\kappa-2)} \\ s_{CH(\kappa-1)} \\ s_{CH\kappa} \end{pmatrix} = \begin{pmatrix} 1 & 0 & 1 & 0 \\ 0 & 1 & 1 & 0 \\ 0 & 1 & 0 & 1 \end{pmatrix} \begin{pmatrix} \rho_{S1} \\ \rho_{S1} \\ \rho_{D1} \\ \rho_{Dv} \end{pmatrix} \quad (15)$$

Herein, while monitoring the observed light amounts of channel CH($\kappa$−1) and channel CH$\kappa$, the optical attenuator connected to the light detection probe D($\nu$−1) is controlled so that $S_{CH(\kappa-1)}$ becomes the observation value/$S_{CH\kappa}$. In this way, a state expressed by the following Expression (16) is achieved.

[Mathematical formula 16]

$$\begin{pmatrix} s_{CH(\kappa-2)} \\ s_{CH(\kappa-1)} \\ s_{CH\kappa} \end{pmatrix} \rightarrow \begin{pmatrix} s_{CH(\kappa-2)} \\ \hat{s}_{CHv} \\ \hat{s}_{CHv} \end{pmatrix} = \begin{pmatrix} 1 & 0 & 1 & 0 \\ 0 & 1 & 1 & 0 \\ 0 & 1 & 0 & 1 \end{pmatrix} \begin{pmatrix} \rho_{S1} \\ \rho_{S1} \\ \rho_{Dv} \\ \rho_{Dv} \end{pmatrix} \quad (16)$$

From Expression (16), it is seen that the following Expression (17) is also valid.

[Mathematical formula 17]

$$S_{CH(\kappa-2)} = S_{CH(\kappa-1)} = S_{CH\kappa} = \rho_{S1} + \rho_{Dv} \quad (17)$$

Accordingly, it is seen that at the same time that the observed light amount is levelled to $e^{(\rho S1 + \rho Dv)}$ from channel CH($\kappa$−2) to channel CH$\kappa$, the effective incident light amounts of all of the light irradiation probes and the effective detection efficiencies of all of the light detection probes are respectively levelled to $e^{\rho S1}$, $e^{\rho Dv}$. By tracing the present operation from channel CH($\nu$−3) to channel CH1, all of the channels from channel CH$\kappa$ to channel CH1 can be levelled to the observed light amount $e^{(\rho S1 + \rho Dv)}$.

With the above-described procedure, it is possible to level the observed light amounts between the light irradiation probe $i_{max}$ having the maximum effective incident light amount and the light detection probe $j_{max}$ having the maximum effective detection efficiency in an arbitrary linked channel group, and to further level the observed light amounts by the adjacent channel levelling operation with respect to all of the channels in the group. In view of the above, the procedure for levelling within a linked channel group is summarized as follows.

First, after the probes have been attached to the head of the subject, the transmittance of all of the optical attenuators on the irradiating side and the detection side are set to approximately 50%, and all of the light source outputs are set to a maximum light amount $I_{safe}$ of light irradiation that is safe with respect to the living body (subject).

Second, the wavelength $\lambda$ is selected, $e^{bi,\lambda}$ and $e^{bj,\lambda}$ of each probe are estimated according to Expression (9) and Expression (10), and the light irradiation probe $i_{max}$ such that $e^{bi,\lambda}$ has a maximum value and the light detection probe $j_{max}$ such that $e^{bj,\lambda}$ has a maximum value are selected.

Third, the adjacent channel levelling operation is performed for the channels on the shortest path connecting the light irradiation probe $i_{max}$ and the light detection probe $j_{max}$, and the observed light amounts are equalized to $e^{(bimax,\lambda + bjmax,\lambda)}$.

Fourth, the adjacent channel levelling operation is performed similarly with respect to a channel adjacent to the channels levelled in the third procedure.

Fifth, the second to fourth procedures are performed with respect to all of the wavelengths being used. Sixth, fNIRS measurement is performed in a state in which the setting determined up to the fifth procedure is maintained. And seventh, the process returns back to the first procedure at the end of the measurement, or all of the light source outputs are shut down.

Minimization of Noise Variance

Figure 5:
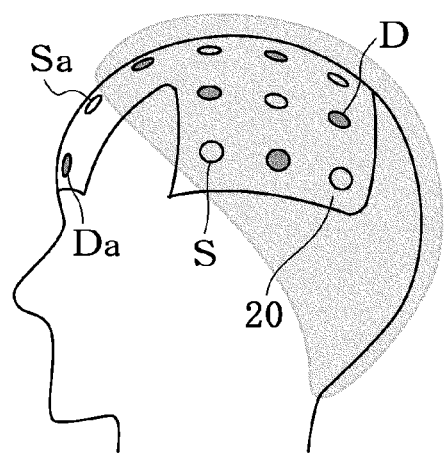
FIG. 5 depicts a second arrangement example of the light irradiation probes S1, S2 and the light detection probes D1, D2 on the holder 20 depicted in FIG. 1.

In order to level the noise variance in accordance with as low a level as possible, it is desirable to provide, for at least one channel of the link group being measured, a light irradiation probe Sa and a light detection probe Da for being arranged in a hairless head portion, such as the forehead, and a light irradiation probe S and a light detection probe D, as depicted in FIG. 5. The reason is as follows.

Because the effective incident light amount and the effective detection efficiency in a channel in the hairless portion are significantly greater than in the hairy portion, and are also temporally constant, the noise variance of the channel is significantly small. Accordingly, by performing the levelling based on probe attachment including the hairless portion and with the channel being used as a reference point, it becomes possible to level all channels to the signal-to-noise ratio of the best level within the range of safe light irradiation intensity.

Next, a noise variance normalizing technique will be described which is useful when it is desired to statistically compare data obtained by performing fNIRS measurement at different dates/times or data obtained with respect to different subjects.

The present technique, which comes down to levelling the noise variance of two independent linked channel groups (non-linked two groups), cannot be implemented by the levelling procedure in the linked channel group. Thus, in the following, methods of noise levelling between only temporally non-linked two groups and noise levelling between temporally and spatially non-linked two groups will be described.

Noise Levelling Between Only Temporally Non-Linked Channel Groups

The only temporally non-linked two groups refer to the case in which, for example, fNIRS measurement is performed at different dates/times with respect to the identical subject or identical site. In the following, an example in which the noise levelling method for two groups in this case is implemented by the control unit 3 depicted in FIG. 1 will be described with reference to FIG. 6. It goes without saying that the brain function measurement method of FIG. 6 is not limited to the case of implementation through control by the control unit 3 depicted in FIG. 1.

Figure 6:
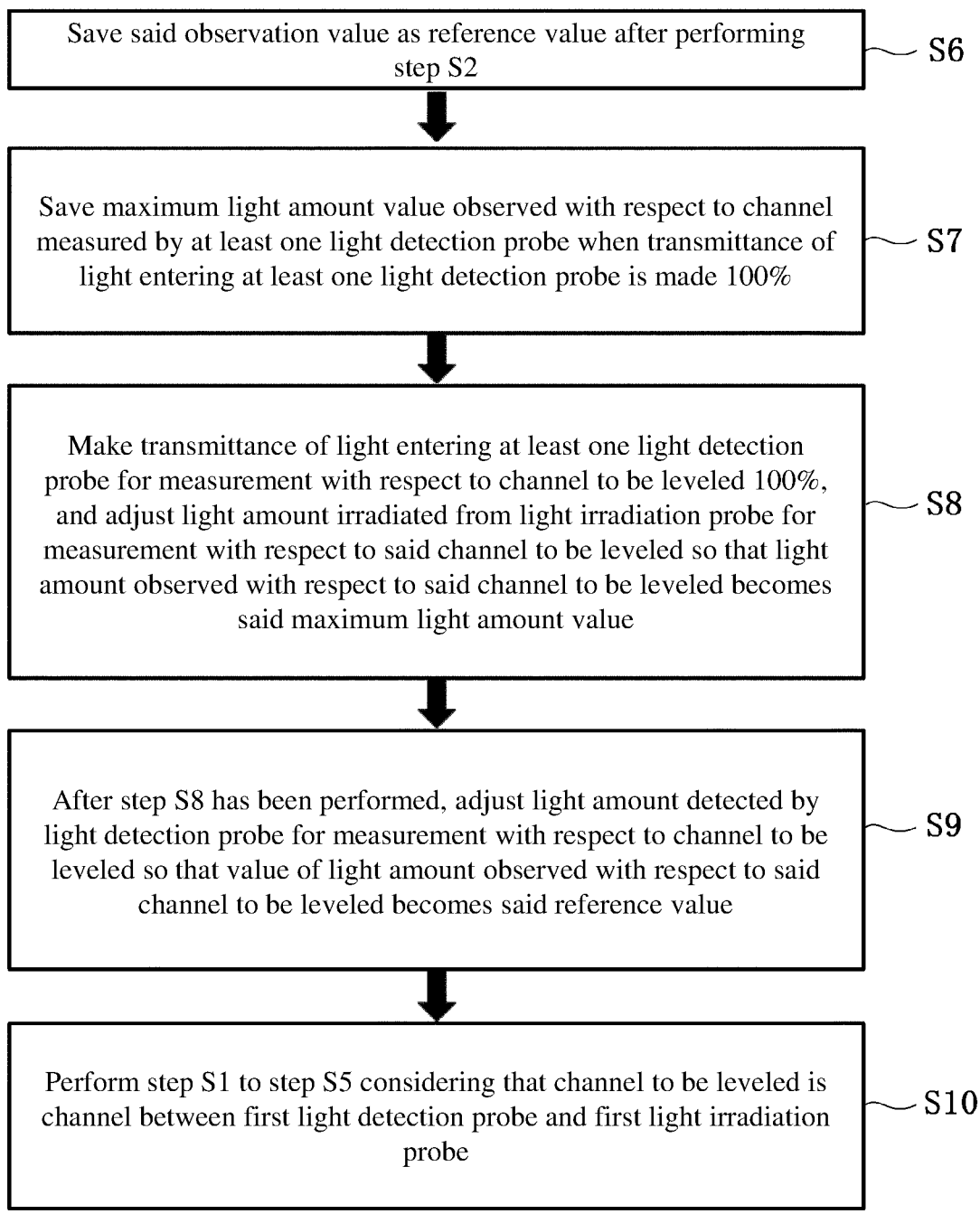
FIG. 6 is a flowchart illustrating a method of implementing a second brain function measurement method according to an embodiment of the present invention through control by the control unit 3 depicted in FIG. 1.

According to the brain function measurement method of FIG. 6, as a premise, the holder 20 is attached to the head of the subject, as depicted in FIG. 5, whereby the light irradiation probe Sa and the light detection probe Da for arranging a channel in a morphologically easily localizable site of a hairless head portion, such as the forehead, and the light irradiation probe S and the light detection probe D are disposed.

Then, initially in step S6, the control unit 3, after performing step S1 and step S2 of FIG. 4, saves the observation value obtained in step S1 in the storage unit 9 as a reference value (reference observed light amount).

Then, in step S7, the control unit 3, during a measurement as a reference at the hairless head portion, such as the forehead, turns off the function of the optical attenuator connected to at least one light detection probe, thereby making the transmittance of light entering the light detection probe 100%. The control unit 3 then saves the maximum light amount value (maximum observed light amount) observed with respect to a channel measured by the at least one light detection probe in the storage unit 9.

Then, in step S8, the control unit 3, in a state in which the function of the optical attenuator connected to at least one light detection probe in an independent channel group to be leveled at the hairless head portion, such as the forehead, is turned off, makes the transmittance of light entering the light detection probe 100%, and adjusts the optical attenuator connected to the light irradiation probe for measurement with respect to the channel to be levelled, so that the light amount observed with respect to the channel corresponds to the maximum light amount value, thereby adjusting the light amount irradiated from the present light irradiation probe.

Then, in step S9, the control unit 3, after performing step S8, adjusts the optical attenuator connected to the light detection probe for measurement with respect to the channel to be leveled so that the value of the light amount observed with respect to the channel corresponds to the reference value, thereby adjusting the light amount detected by the light detection probe. At this stage, the effective incident light amount and the effective detection efficiency of the channel respectively correspond to the values of the effective incident light amount and the effective detection efficiency in the channel group as the levelling reference.

Next, in step S10, the control unit 3, assuming that the channel to be leveled corresponds to the channel between the first light detection probe and the first light irradiation probe depicted in FIG. 4, performs step S1 to step S5 of FIG. 4. As a result of this step, the noise variance of the channel group comes to correspond to the noise variance of the channel group as the levelling reference.

In the following, it will be described how, with the brain function measurement method of FIG. 6, levelling of non-linked two groups is implemented. When the reference observed light amount and the maximum observed light amount obtained in step S6 and step S7 of FIG. 6 are $J^{(1)}$, $J^{(2)}$, respectively, log $J^{(1)}$ is $S^{(1)}$, and log $J^{(2)}$ is $S^{(2)}$, the following Expression (18) and Expression (19) are valid.

[Mathematical formula 18]

$$S^{(1)} = \rho i_{max} + \rho j_{max} \quad (18)$$

[Mathematical formula 19]

$$S^{(2)} = \rho i_{max} + \rho j^0 \quad (19)$$

Herein, $\rho j^0$ of Expression (19) is the logarithm of the effective detection efficiency at the time of measuring the maximum observed light amount, when the function of the optical attenuator connected to the light detection probe is turned off and the optical transmittance is made 100%. When the channel of another link group which is independent of the reference link group and attached to the hairless portion is CH, and the light irradiation probe and the light detection probe constituting the channel are respectively s, d, the following Expression (20) is valid.

[Mathematical formula 20]

$$S_{CH} = \rho s + \rho d \quad (20)$$

Herein, if, according to step S7, the function of the optical attenuator connected to the light detection probe d for measuring the channel CH is turned off, $\rho d$ of Expression (20) corresponds to $\rho j^0$ in view of the constancy of observation at the hairless head portion as mentioned in the second paragraph under the section entitled "Minimization of Noise Variance". Accordingly, the following Expression (21) is valid.

[Mathematical formula 21]

$$S_{CH} = \rho s + \rho j^0 \quad (21)$$

Further, it is seen that by adjusting the optical attenuator connected to the light irradiation probe such that $S_{CH}$ becomes $S^{(2)}$, as described in step S8, $\rho s$ can be made $\rho i_{max}$ from a comparison of Expression (19) and Expression (21). In this case, the following Expression (22) is valid.

[Mathematical formula 22]

$$S_{CH} = \rho i_{max} + \rho j^0 \quad (22)$$

Further, it is seen that by adjusting the optical attenuator connected to the light detection probe such that $S_{CH}$ becomes $S^{(1)}$ as described in step S9, $\rho j^0$ can be made $\rho j_{max}$ from a comparison of Expression (18) and Expression (22). In this case, the following Expression (23) is valid.

[Mathematical formula 23]

$$S_{CH} \rho i_M = \rho j_{max} \quad (23)$$

Then, by performing levelling by the method of FIG. 4 using the channel as a reference point, it becomes possible to level the channels in a single link group to the noise variance of the reference link group.

Noise Levelling Between Temporally and Spatially Non-Linked Channel Groups

When performing measurement of the top of the head in which motor-related areas and the like are positioned, it is often inefficient to arrange the reference-point channel at the forehead as described above, for example, because of the distance from the position to be measured. Meanwhile, in the absence of a spatially common reference point, the two groups become non-linked not only temporally but also spatially.

Accordingly, in the following, an example in which a method of performing noise levelling for temporally and spatially non-linked two groups is implemented through control by the control unit 3 as depicted in FIG. 1 will be described with reference to FIG. 7.

Figure 7:
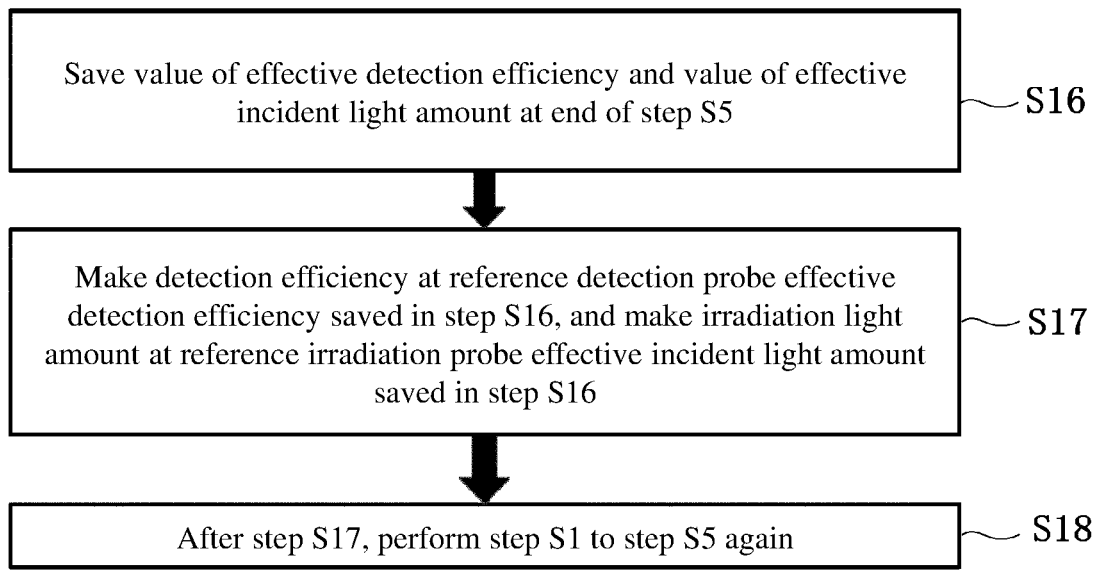
FIG. 7 is a flowchart illustrating a method of implementing a third brain function measurement method according to an embodiment of the present invention through control by the control unit 3 depicted in FIG. 1.

It goes without saying that the brain function measurement method of FIG. 7 is not limited to the case of implementation through control by the control unit 3 depicted in FIG. 1.

Figure 8:
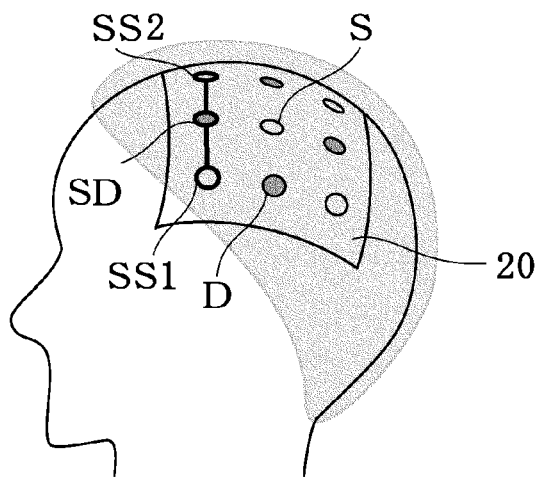
FIG. 8 depicts a third arrangement example of the light irradiation probes S1, S2 and the light detection probes D1, D2 on the holder 20 depicted in FIG. 1.

According to the brain function measurement method of FIG. 7, as a premise, designated value-controllable optical attenuators are only connected to three probes constituting specific two reference channels adjacent to each other in a link group, as depicted in FIG. 8, i.e., only to reference irradiation probes SS1, SS2 and a reference detection probe SD; and the control unit 3 adjusts each of the optical attenuators so that the transmittances of the optical attenuators become designated values.

Figure 9:
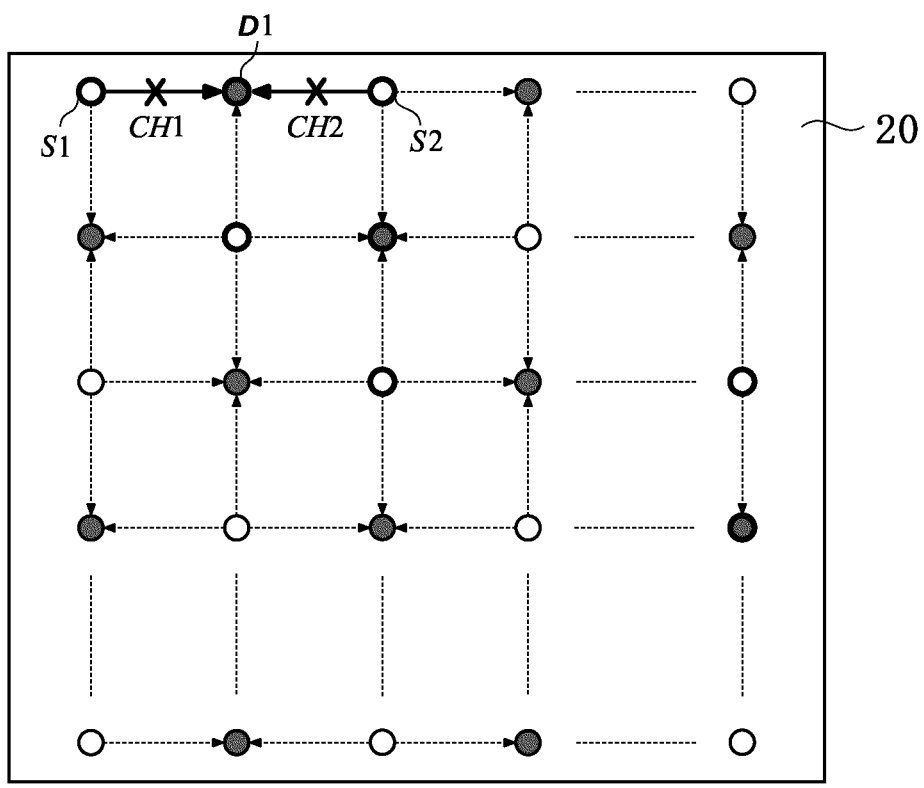
FIG. 9 is a schematic diagram depicting the arrangement of the light irradiation probes and the light detection probes depicted in FIG. 8 in a two-dimensional plane.

FIG. 9 is a schematic diagram illustrating the arrangement of the light irradiation probes and the light detection probes of FIG. 8 in a two-dimensional plane. The light irradiation probe S1 of FIG. 9 corresponds to the reference irradiation probe SS1, and the light irradiation probe S2 of FIG. 9 corresponds to the reference irradiation probe SS2. The light detection probe D1 of FIG. 9 corresponds to the reference detection probe SD. The channels CH1, CH2 of FIG. 9 correspond to the two reference channels.

First, in step S16, the control unit 3, with respect to measurement of linked multiple channels including the reference channels SCH1, SCH2, performs noise levelling by applying the method of FIG. 4, and saves the obtained values of effective detection efficiency and effective incident light amount in the storage unit 9.

Then, when linked multiple-channel measurement has been performed at another date/time or in a different position, the control unit 3 in step S17 controls the optical attenuator connected to the reference detection probe SD, and thereby makes the detection efficiency at the reference detection probe SD the effective detection efficiency saved in step S16. The control unit 3 also controls the optical attenuators connected to the reference irradiation probes SS1, SS2, and thereby makes the irradiation light amount at the reference irradiation probes SS1, SS2 the effective incident light amount saved in step S16.

Then, in step S18, the control unit 3, after step S17, again performs step S1 to step S5 of FIG. 4, i.e., the adjacent channel levelling operation, from the reference channels SCH1, SCH2 as reference points, and performs noise levelling with respect to all of the channels in the linked channel group.

In the following, with reference to FIG. 9, the control method in step S17 will be described concretely. With respect to the channels CH1, CH2 depicted in FIG. 9, i.e., the light irradiation probes S1, S2 and the light detection probe D1, the following Expression (24) is valid.

[Mathematical formula 24]

$$\begin{pmatrix} s_{CH1} \\ s_{CH2} \end{pmatrix} = \begin{pmatrix} 1 & 0 & 1 \\ 0 & 1 & 1 \end{pmatrix} \begin{pmatrix} \rho_{S1} \\ \rho_{S2} \\ \rho_{D1} \end{pmatrix} \quad (24)$$

By subjecting Expression (24) to general inverse matrix computation of the probe arrangement matrix, the following Expression (25) is obtained.

[Mathematical formula 25]

$$\begin{pmatrix} \rho_{S1} \\ \rho_{S2} \\ \rho_{D1} \end{pmatrix} = \begin{pmatrix} 1 & 0 & 1 \\ 0 & 1 & 1 \end{pmatrix}^{+} \begin{pmatrix} s_{CH1} \\ s_{CH2} \end{pmatrix} \quad (25)$$

In each channel of the reference link group for which levelling has been completed, Expression (23) is valid. Further, when designated value-controllable elements as described above are used, it is possible to obtain the transmittance ax of the optical attenuator connected to the probe x providing ρx, concretely according to Expression (7). This indicates that in order to make $\rho_{S1}$ $\rho_{imax}$ and $\rho_{D1}$ $\rho_{jmax}$, the transmittance $a_{S1}$ may be multiplied by $e^{(\rho imax - \rho S1)}$ and the transmittance $a_{D1}$ by $e^{(\rho jmax - \rho D1)}$.

In Expression (24) and FIG. 9, as the reference detection probe and the reference irradiation probes, one light detection probe D1 and two light irradiation probes S1, S2 sandwiching the same are used, respectively. Instead, one light irradiation probe and two light detection probes sandwiching the same may be used, in which case it is possible to level the link group by the same method.

With the brain function measurement device according to the embodiment of the present invention, and with a brain function measurement system and a brain function measurement method incorporating the device, it is possible to eliminate or minimize the need for a calibration operation for the device. That is, the noise of all of the channels in a linked channel group can be leveled without adjusting the transmittance of an optical attenuator to a designated value.

More specifically, according to the methods of FIG. 4 and FIG. 6, the need for calibration of the optical attenuator is eliminated. Meanwhile, according to the method of FIG. 7, while it is necessary to use designated value-controllable optical attenuators in three probes, it is sufficient in this case, too, if only three designated value-controllable optical attenuators are connected to the three probes, no matter how large the number of channels becomes. Accordingly, it is possible to greatly simplify the adjustment or maintenance of the brain function measurement device or a system including the device, and to achieve size reduction.

In another aspect, with the brain function measurement device according to the embodiment of the present invention and the brain function measurement system or the brain function measurement method incorporating the device, it is possible to level noise variance between a plurality of independent link groups. The method includes a method by which, as indicated in FIG. 6, a reference point at which the noise variance can be assumed to be temporally invariable is commonly set between groups, and a method by which, as indicated in FIG. 7, designated value-controllable optical attenuators are used only in probes constituting two channels adjacent to each other in one group.

Both of the methods make it possible to perform statistical comparison of chronological changes in data of a single subject. In addition, the latter method makes it possible to perform statistical comparison with respect to measurements pertaining to a plurality of subjects or at a plurality of sites of the head.

Further, in yet another aspect, with the brain function measurement device according to the embodiment of the present invention and the brain function measurement system or the brain function measurement method incorporating the device, it is possible, by using a channel placed in a hairless portion as a levelling reference point, to level noise variance in measurements at any sites that can be linked or at any date/time, in accordance with the level of the hairless portion. Accordingly, it is possible to obtain a maximum achievable signal-to-noise ratio steadily, while observing a safe range of light irradiation intensity.

REFERENCE SIGNS LIST

1 Brain function measurement device
3 Control unit
5 Light source unit
7 Data measurement unit
9 Storage unit
11 to 14 Optical attenuator
S, S1, S2 Light irradiation probe
D, D1 to D3 Light detection probe
SS1, SS2 Reference irradiation probe
SD Reference detection probe

The invention claimed is:

1. A brain function measurement device comprising:
a first irradiation means for irradiating a brain of a subject with light;
a first detection means disposed adjacent to the first irradiation means, the first detection means for detecting light reflected by the brain among the light irradiated from the first irradiation means;
a second irradiation means disposed adjacent to the first detection means, the second irradiation means for irradiating the brain of the subject with light;
a second detection means disposed adjacent to the second irradiation means, the second detection means for detecting light reflected by the brain among the light irradiated from the second irradiation means; and
a control means for performing a first adjustment of a light amount irradiated by the second irradiation means so that a light amount measured at a measurement point between the first detection means and the second irradiation means becomes an observation value observed at a measurement point between the first irradiation means and the first detection means, the control means further for performing a second adjustment of a light amount detected by the second detection means so that a light amount measured at a measurement point between the second irradiation means and the second detection means becomes the observation value.

2. The brain function measurement device according to claim 1, comprising a plurality of irradiation means and a plurality of detection means, the plurality of irradiation means comprising the first irradiation means and the second irradiation means, and the plurality of detection means comprising the first detection means and the second detection means, wherein the control means is configured to:
select, from among the plurality of irradiation means, an irradiation means having a maximum effective incident light amount;
select, from among the plurality of detection means, a detection means having a maximum effective detection efficiency;
perform, at each measurement point of a plurality of measurement points positioned on a shortest path connecting the irradiation means and the detection means that have been selected, the first adjustment and the second adjustment in an order from the irradiation means to the detection means that have been selected; and
perform, at each measurement point of the plurality of measurement points positioned on the shortest path, the second adjustment and the first adjustment in an order from the detection means to the irradiation means that have been selected.

3. The brain function measurement device according to claim 2, wherein the control means is configured to perform the first adjustment and the second adjustment, and the second adjustment and the first adjustment, for each and every wavelength irradiated.

4. The brain function measurement device according to claim 2, wherein at least one of the plurality of measurement points irradiated by the irradiation means having the maximum effective incident light amount and the measurement point detected by the detection means having the maximum effective detection efficiency is configured to be disposed in a hairless portion of the subject.

5. The brain function measurement device according to claim 4, further comprising a storage means, wherein the control means is further configured to:
  adjust the light amount irradiated by the second irradiation means so that the light amount measured at the measurement point between the first detection means and the second irradiation means becomes the observation value observed at the measurement point between the first irradiation means and the first detection means;
  adjust the light amount detected by the second detection means so that the light amount measured at the measurement point between the second irradiation means and the second detection means becomes the observation value, then save the observation value in the storage means as a reference value, and save a maximum light amount value observed at the measurement point measured by at least one of the plurality of detection means in the storage means when the transmittance of light entering the at least one of the plurality of detection means is made 100%; and
  make the transmittance of light entering the at least one of the plurality of the detection means for measurement at the measurement point to be leveled 100%, adjust the light amount irradiated from the irradiation means for measurement at the measurement point to be leveled so that the light amount observed at the measurement point to be leveled becomes the maximum light amount value, then adjust the light amount detected by the detection means for measurement at the measurement point to be leveled so that a value of the light amount observed at the measurement point to be leveled becomes the reference value, and perform adjustment of the irradiation means on the assumption that the measurement point to be leveled is a measurement point between the first detection means and the first irradiation means.

6. The brain function measurement device according to claim 2, further comprising a storage means, wherein the control means is further configured to:
  save, in the storage means, a value of effective detection efficiency of the first detection means and a value of effective incident light amount of the first irradiation means at a point in time when the light amount irradiated by the second irradiation means has been adjusted so that the light amount measured at the measurement point between the first detection means and the second irradiation means becomes the observation value observed at the measurement point between the first irradiation means and the first detection means, and when the light amount detected by the second detection means has been adjusted so that the light amount measured at the measurement point between the second irradiation means and the second detection means becomes the observation value; and
  make the detection efficiency at the first detection means the effective detection efficiency that has been saved, make the irradiation light amount at the first irradiation means the effective incident light amount that has been saved, and again perform the adjustment with respect to the irradiation means.

7. A method of measuring brain function by irradiating a brain of a subject with light and detecting light reflected by the brain, the method comprising:
  a first step of adjusting a light amount irradiated by a second irradiation means so that a light amount measured at a measurement point between a first detection means and the second irradiation means adjacent to each other becomes an observation value observed at a measurement point between a first irradiation means adjacent to the first detection means; and
  a second step of adjusting a light amount detected by the second detection means so that a light amount measured at a measurement point between the second irradiation means and a second detection means adjacent to the second irradiation means becomes the observation value.

8. The method according to claim 7, wherein the method measures the brain function at a plurality of measurement points, the method further comprising:
  a third step of selecting an irradiation means from among a plurality of irradiation means that has a maximum effective incident light amount, and selecting a detection means from among a plurality of detection means that has a maximum effective detection efficiency, the plurality of irradiation means comprising the first irradiation means and the second irradiation means, and the plurality of detection means comprising the first detection means and the second detection means;
  a fourth step of, at each measurement point of the plurality of measurement points positioned on a shortest path connecting the irradiation means and the detection means that have been selected, performing the first step and second step in an order from the irradiation means to the detection means that have been selected, and then, at each measurement point of the plurality of measurement points positioned on the shortest path, performing the second step and first step in an order from the detection means to the irradiation means that have been selected; and
  a fifth step of performing the first step and the second step between each measurement point of the plurality of measurement points positioned on the shortest path and a measurement point adjacent to each measurement point of the plurality of measurement points.

9. The method according to claim 8, wherein the third step to the fifth step are performed for each and every wavelength irradiated.

10. The method according to claim 8, wherein at least one of the plurality of measurement points irradiated by the irradiation means having the maximum effective incident light amount and the measurement point detected by the detection means having the maximum effective detection efficiency is disposed in a hairless portion of the subject.

11. The method according to claim 10, further comprising:
  a sixth step of saving the observation value as a reference value after the second step has been performed;

a seventh step of saving a maximum light amount value observed at the measurement point measured by at least one of the plurality of detection means when the transmittance of light entering the at least one of the plurality of detection means is made 100%;

an eighth step of making the transmittance of light entering the at least one of the plurality of detection means for measurement at the measurement point to be leveled 100%, and adjusting the light amount irradiated from the irradiation means for measurement at the measurement point to be leveled so that the light amount observed with respect to the measurement point to be leveled becomes the maximum light amount value;

a ninth step of, after the eighth step has been performed, adjusting the light amount detected by the detection means for measurement at the measurement point to be leveled so that a value of the light amount observed at the measurement point to be leveled becomes the reference value; and a tenth step of performing the first step to the fifth step, assuming that the measurement point to be leveled is the measurement point between the first detection means and the first irradiation means.

12. The method according to claim 8, further comprising:

a sixth step of saving a value of the effective detection efficiency and a value of the effective incident light amount at a point in time when the fifth step has been completed; and a seventh step of making a detection efficiency at the detection means for measuring two measurement points of the plurality of measurement points adjacent to each other the effective detection efficiency saved in the sixth step, and making an irradiation light amount at the irradiation means for measuring the two measurement points the effective incident light amount that has been saved in the sixth step, wherein, after the seventh step, the first step to the fifth step are performed again, using the two measurement points of the plurality of measurement points.

* * * * *